United States Patent

Oftring et al.

[11] Patent Number: 5,082,599
[45] Date of Patent: Jan. 21, 1992

[54] 2-METHYL- AND 2-HYDROXYMETHYL-SERINE-N,N-DIACETIC ACID AND DERIVATIVES THEREOF

[75] Inventors: Alfred Oftring, Bad Duerkheim; Stefan Birnbach, Ludwigshafen; Richard Baur, Mutterstadt; Charalampos Gousetis; Wolfgang Trieselt, both of Ludwigshafen, all of Fed. Rep. of Germany

[73] Assignee: BASF Aktiengesellschaft, Ludwigshafen, Fed. Rep. of Germany

[21] Appl. No.: 494,308

[22] Filed: Mar. 16, 1990

[30] Foreign Application Priority Data

May 6, 1989 [DE] Fed. Rep. of Germany ....... 3914980

[51] Int. Cl.$^5$ .................... C02F 5/02; C02F 5/08; C11D 3/26
[52] U.S. Cl. .................... 252/546; 252/180; 252/DIG. 11; 252/178; 252/81; 562/568
[58] Field of Search ............... 562/568; 252/546, 175, 252/180, DIG. 11, 81, 178

[56] References Cited

U.S. PATENT DOCUMENTS

| | | | |
|---|---|---|---|
| 2,316,636 | 4/1943 | Teeters | 562/568 |
| 2,401,196 | 5/1946 | Senkus | 562/568 |
| 2,500,019 | 3/1950 | Bersworth | 562/568 |
| 2,781,392 | 2/1957 | Mannheimer | 562/568 |
| 3,056,799 | 10/1962 | Tullar | 562/568 |
| 3,293,176 | 12/1966 | White | 562/568 |
| 3,580,950 | 5/1971 | Bersworth | 562/568 |
| 4,827,014 | 5/1989 | Baur et al. | 252/180 |
| 4,973,730 | 11/1990 | Baur et al. | 562/568 |

FOREIGN PATENT DOCUMENTS

| | | | |
|---|---|---|---|
| 141938 | 7/1948 | Australia | 252/546 |
| 725212 | 1/1966 | Canada | 562/568 |
| 2401752 | 7/1974 | Fed. Rep. of Germany | 252/546 |
| 3712330 | 10/1988 | Fed. Rep. of Germany | 562/568 |
| 122747 | 9/1980 | Japan | 562/568 |
| 989926 | 4/1965 | United Kingdom | 562/568 |

Primary Examiner—Prince Willis, Jr.
Assistant Examiner—J. Silbermann
Attorney, Agent, or Firm—Oblon, Spivak, McClelland, Maier & Neustadt

[57] ABSTRACT

2-Methyl- and 2-hydroxymethyl-serine-N,N-diacetic acid and derivatives thereof of the general formula I

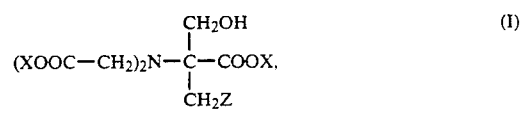

in which X denotes hydrogen, alkali metal or ammonium which may or may not be substituted by $C_1$–$C_4$-hydroxyalkyl groups and Z denotes hydrogen or hydroxyl.

The compounds I serve as complexing agents for heavy metal ions or alkaline earth metal ions and as bleach stabilizers or builders in detergents and cleaning formulations.

5 Claims, No Drawings

2-METHYL- AND 2-HYDROXYMETHYL-SERINE-N,N-DIACETIC ACID AND DERIVATIVES THEREOF

The present invention relates to 2-methyl- and 2-hydroxymethyl-serine-N,N-diacetic acid and derivatives thereof of the general formula I

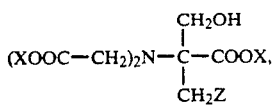

in which X denotes hydrogen, alkali metal or ammonium which may or may not be substituted by $C_1$-$C_4$-alkyl or $C_1$-$C_4$-hydroxyalkyl groups and Z denotes hydrogen or hydroxyl. The invention further relates to a process for the manufacture of compounds I and to their use as complexing agents for heavy metal ions or alkaline earth metal ions and as bleach stabilizers or builders in detergents and cleaning compositions and to corresponding formulations containing said compounds I.

The general teaching of EP-A 001,310 relates to detergent compositions consisting of anionic, non-ionic, amphoteric or dipolar detergents, polyphosphonates and compounds containing carboxyl groups, and the general formula given for the last-named compounds includes the above serine derivatives I, although no further disclosure concerning the same is made.

Erdey describes the complexing properties of D,L-serine-N,N-diacetic acid in Acta Chim. Hung., Vol 21, 1959, pp. 327-332. The complexes with alkaline earth metal ions referred to therein are stated to be less stable than, for example, corresponding complexes with nitrilotriacetic acid.

It is thus an object of the present invention to provide novel complexing agents for heavy metal ions and alkaline earth metal ions for a wide variety of industrial applications, which agents not only have good complexing properties but are also ecologically acceptable, i.e. show good biological degradability.

Accordingly, we have found the 2-methyl- and 2-hydroxymethyl-serine-N,N-diacetic acids and their derivatives as defined above.

Compounds I may occur as free carboxylic acids (X=H) or partially or totally in salt form. In the latter case X will stand for an alkali metal ion such as lithium or, in particular, sodium or potassium, or for an ammonium ion, which may be partially or totally substituted by $C_1$-$C_4$-alkyl ion such as lithium or, in particular, sodium or potassium, or for an ammonium ion, which may be partially or totally substituted by $C_1$-$C_4$-alkyl groups or $C_1$-$C_4$-hydroxyalkyl groups. Particularly noteworthy in this respect are triamine salts having tertiary nitrogen atoms and based on amine bases such as trimethylamine, triethylamine, tri-n-propylamine, triisopropylamine, tri-n-butylamine and triisobutylamine or on trialkanolamines such as triethanolamine and triisopropylamine.

The compounds I are advantageously prepared by any one of the four procedures (a) to (d) described below.

In procedure (a), amines of the general formula II

in which Y denotes any of the groups COOR, $CONH_2$ and CN, R standing for hydrogen, alkali metal such as sodium or potassium, ammonium or a $C_1$-$C_4$-alkyl radical such as methyl, ethyl, n-propyl, isopropyl, n-butyl and t-butyl, is reacted with formaldehyde and hydrogen cyanide or an alkali metal cyanide such as sodium or potassium cyanide to form 2-methyl- or 2-hydroxymethyl-serine-N,N-diacetonitrile or derivatives thereof of the general formula V:

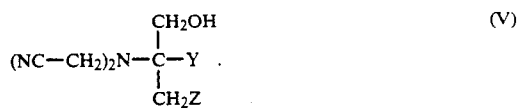

The preferred starting material II is 2-methyl- or 2-hydroxymethyl-serine in the form of a mixture of its racemic forms. It is also advantageous to use its sodium, potassium or ammonium salt.

This reaction is effected in conventional manner following the lines of the Strecker synthesis as described, for example, in Houben-Weyl: Methoden der Organischen Chemie, Vol. 11/2. pp. 408-412, 1958, Thieme-Verlag, Stuttgart for diamines, carbonyl compounds and aqueous hydrogen cyanide solutions.

The reaction is preferably carried out in water, but it may also be effected in an organic solvent or a mixture thereof with water. Preferred organic solvents are those such as are partially or totally miscible with water, for example methanol, ethanol, n-propanol, isopropanol, t-butanol, dioxane and tetrahydrofuran.

It is convenient to use, per mole of compound II, from 2 to 2.6 moles of formaldehyde, preferably in the form of an approx. 30% w/w solution in water, and from 2 to 2.3 moles of hydrogen cyanide or alkali metal cyanide. The reaction is normally carried out at a temperature of from 0° to 45° C. and in particular from 15° to 25° C. when anhydrous hydrogen cyanide is used, or at a temperature of from 40° to 100° C. and in particular from 70° to 100° C. when an alkali metal cyanide is used. The reaction with anhydrous hydrogen cyanide is usually carried out at a pH of from 0 to 11 and in particular from 3 to 9.

The conversion of compound II to the intermediate V is conveniently followed by a stage in which carboxamide and nitrile groups still present are hydrolyzed to carboxyl groups, this being effected in conventional manner in an aqueous reaction medium in the presence of a base such as caustic soda or caustic potash or an acid such as sulfuric or hydrochloric acid at a temperature of from 20° to 110° C. and in particular from 40° to 100° C.

Depending on the reaction conditions used, the compound I is obtained as a free carboxylic acid or, for example, as an alkali metal salt. The free acid may be readily converted to a desired salt I by neutralization with an appropriate base such as an amine base.

The isolation of the pure compound of formula I from its solution is unproblematic. Particularly suitable methods are spray drying, freeze drying, crystallization and precipitation. For some industrial applications, it may be advantageous to proceed with the solution in unchanged form following the above synthesis.

In procedure (b), an amine of formula II is reacted in known manner with a monohalo-acetic acid or a $C_1$–$C_4$-alkyl ester thereof or with a monohalo-acetonitrile to form compound V or an analogue thereof. A suitable monohalo-acetic acid or derivative is chloro-acetic acid, methyl chloro-acetate, ethyl chloro-acetate, propyl chloro-acetate, butyl chloro-acetate, chloro-acetonitrile and the bromine analogues.

As in procedure (a), it is preferred to operate in water or, alternatively, in an organic solvent or mixture thereof with water. Conveniently, from 2 to 2.6 moles of monohalo-acetic acid or a derivative thereof are reacted with 1 mole of amine II at a temperature of from 0° to 100° C. and in particular from 40° to 80° C., at a pH of from 7 to 14 and in particular from 7.5 to 12. The reaction will usually be carried out in aqueous sodium or potassium hydroxide solution or in the presence of an acid-binding substance such as a tertiary amine, for example trimethylamine, triethylamine, tri-n-propylamine, triisopropylamine, tri-n-butylamine, triisobutylamine or 1,4-diazabicyclo[2.2.2]octane.

Subsequent hydrolysis of any carboxamide, carboxylate or nitrile groups still present and workup of the compounds I obtained are conveniently carried out as in procedure (a) above.

In procedure (c), hydroxyacetone or 1,3-dihydroxyacetone is reacted with an imino compound of the general formula III:

$$(Y-CH_2)_2NH \qquad (III)$$

and hydrogen cyanide or an alkali metal cyanide, in known manner, to form a serinenitrile derivative of the general formula Va:

$$(Y-CH_2)_2N-\underset{\underset{CH_2Z}{|}}{\overset{\overset{CH_2OH}{|}}{C}}-CN. \qquad (Va)$$

Examples of suitable imino compounds III are imino-diacetic acid and the mono- and di-sodium salts thereof, the mono- and di-potassium salts thereof and the mono- and di-ammonium salts thereof, imino-diacetamide, imino-diacetonitrile, mono- and di-methyl imino-diacetates and mono- and di-ethyl imino-diacetates.

The reaction is preferably carried out in water, as in procedure (a), but it is also possible to operate in an organic solvent or a mixture thereof with water. The hydroxy- or dihydroxy-acetone, the imino compound III and the hydrogen cyanide or alkali metal cyanide are conveniently used in a molar or near molar ratio. The reaction will normally be carried out at a temperature of from 10° to 100° C. and in particular from 10° to 60° C. and at a pH of from 0.5 to 9.

In a preferred embodiment of procedure (c) the hydroxy- or dihydroxy-acetone is first reacted with the imino compound III and then with hydrogen cyanide or alkali metal cyanide. Alternatively, the order of these steps may be reversed. In the event of Z being a hydroxyl group, procedure (d) may be employed, in which nitrilotriacetonitrile is reacted with formaldehyde in known manner.

This reaction is preferably carried out in a lower alcohol such as methanol, ethanol, isopropanol and n-butanol or in water, but it is also possible to operate in an ether such as tetrahydrofuran or dioxane or in a mixture of the above solvents. The formaldehyde is preferably used in the form of an approx. 30% w/w aqueous solution usually in an amount of from 2 to 5 moles and preferably from 2 to 3 moles, per mole of nitrilotriacetonitrile. The reaction will normally be carried out in the presence of a base at a pH of from 7.5 to 12 and in particular from 8.5 to 11 and at a temperature of from 0° to 100° C., in particular from 25° to 80° C.

Suitable bases for this purpose are, for example, tertiary aliphatic amines, in particular trialkylamines such as triethylamine and trialkanolamines such as triethanolamine, alkaline earth metal hydroxides such as sodium or potassium hydroxide, alkali metal carbonates such as sodium or potassium carbonate, and strongly basic synthetic resin ion exchangers in the —OH form.

Subsequent hydrolysis of the nitrile groups present in the intermediate V (Y=CN, Z=OH) and workup of the compounds I obtained are conveniently carried out as in procedure (a) above.

The compounds I of the invention are exceptionally well suited for complexing heavy metal ions and alkaline earth metal ions, such as iron, copper, manganese, zinc, calcium and magnesium or a mixture of said ions. This property makes them suitable for numerous industrial applications. Since the compounds I of the invention are biologically degradable substances, they can be used to advantage wherever the application involves major amounts of waste water requiring clarification before it is recycled to surface water.

Examples of suitable uses and areas of application are detergents, cleaning compositions, industrial cleansers, electroplating, water treatment, polymerizations, the photographic, textile and paper industries and various applications in pharmaceutics, cosmetics, food and plant nutrition.

Another advantage of the said compounds is that they are effective as stabilizers for bleaches, for example sodium perborates such as $NaBo_2.H_2O_2.3H_2O$, peroxycarbonates, peroxyphosphonates, citrate perhydrates, urea/$H_2O_2$ and melamine/$H_2O_2$ adducts, caroates, perbenzoates, peroxyphthalates and alkali metal hypochlorites in detergents and cleaning compositions and for hydrogen peroxide bleaches used for bleaching textiles, cellulose and pulp. Traces of heavy metals such as iron, copper and manganese occur in the detergents themselves and in water and textiles and catalyze decomposition of the per-compounds or the hydrogen peroxide formed therefrom. The complexing agents I of the invention bind said metal ions and prevent decomposition of the bleaching system during storage or in the washing liquid. This increases the efficiency of the bleaching system and inhibits damage to the fibers.

In liquid detergent formulations, the novel complexing agents I may be used as so-called preservatives, advantageously in a concentration of from 0.05 to 1% w/w based on the total weight of the detergent formulation.

Used in soaps, the novel complexing agents I prevent, for example, decomposition due to metal-catalyzed oxidation.

They also serve as exceptionally good builders in detergents and cleaning compositions for the prevention of deposits and incrustations on the fabric.

They may also be used to advantage wherever, in industrial plant, precipitation of calcium, magnesium and heavy metal salts is a disturbing factor which it is necessary to eradicate, for example, deposits and incrustations occurring in boilers, pipes, spray nozzles and, generally, on all smooth surfaces.

They may be used for stabilizing phosphates in alkaline degreasing baths and for preventing precipitation of calcium soaps and thus for preventing "tarnishing" of non-ferrous surfaces and prolonging the useful life of alkaline cleansing baths.

They may be used as complexing agents in alkaline derusting and descaling liquors and in electroplating baths in place of cyanides.

When cooling water is treated with the novel complexing agents I, no deposits occur and any existing deposits are redissolved. The possibility of their use in alkaline media is particularly advantageous for overcoming corrosion problems.

When cooling water is treated with the novel complexing agents I, no deposits occur and any existing deposits are redissolved. The possibility of their use in alkaline media is particularly advantageous for overcoming corrosion problems.

They may be used for the preparation of the redox catalysts employed in the polymerization of rubber, in which case they additionally prevent precipitation of iron hydroxide in the alkaline polymerization medium.

The novel complexing agents may also be used in the photographic industry for preventing precipitation of hardly soluble calcium and magnesium salts in developing and fixing baths made up with hard water. Such precipitation causes fogging of films and prints and forms deposits in tanks, all of which can now be prevented in an advantageous manner. They can also be used to advantage as iron (III) complexing solutions in photographic bleach baths and bleach fixing baths, thus replacing hexacyanoferrate solutions, which are less desirable for ecological reasons.

In the textile industry, they can be used for removing traces of heavy metal during manufacture or dyeing of natural or synthetic fibers. This overcomes a number of problems, such as the occurrence of dirt marks or streaks in the fabric, loss of luster, poor wettability, uneven colorations and color defects.

In the paper industry they are useful for eliminating heavy metal ions, particularly iron ions. The deposition of iron on paper causes "hot spots" where the catalytic destruction of the cellulose due to oxidation begins. Heavy metal ions also catalyze decomposition of $H_2O_2$ used for bleaching paper.

Other applications, for example, relate to pharmaceutics, cosmetics and foodstuffs for preventing metal-catalyzed oxidation of olefinic double bonds and consequent rancidity of the products.

In plant nutrition applications, copper, iron, manganese and zinc complexes with compounds I are used to make up deficiencies of heavy metals. These heavy metals are added in the form of chelates in order to prevent precipitation thereof in the form of biologically inactive, insoluble salts.

Other fields of application for the novel complexing agents I include the washing of exhaust gases, i.e. simultaneous removal of $NO_x$ and $SO_2$. Among the above areas of application, the novel compounds I of the invention, with their excellent complexing properties, are to be highly recommended for use as bleach stabilizers and builders in detergents and cleaning compositions.

The present invention also relates to agents for complexing heavy metal ions and alkaline earth metal ions or mixtures thereof and containing, according to use, from 0.01 to 99% w/w of compound(s) I weight of the composition.

The present invention further relates to detergents and cleaning compositions containing from 0.01 to 20% and preferably from 0.05 to 10%, by weight of the total composition, of one or more of said compounds I of the invention. When used preferentially as builders, a concentration of from 1 to 10% w/w is preferred, and when used preferentially as bleach stabilizers, for example for perborates, a concentration of from 0.05 to 1% w/w is particularly preferred. When used, in particular, as complexing agent in detergents, a concentration of from 0.1 to 2% w/w is preferred.

The compounds I of the invention may be used in their capacity as complexing agents, builders and bleach stabilizers in detergent and cleaning formulations together with other agents known in the art, which in some instances affords distinct improvement of general properties relating to sequestering, inhibition of incrustation, inhibition of graying, primary washing efficiency and bleaching effect.

Detergent and cleaning compositions containing compound(s) I of the invention usually contain, as additional ingredients, from 6 to 25% of surfactants, from 15 to 50% of builders and, possibly, co-builders and from 5 to 30% of auxiliaries such as enzymes, foam regulators, corrosion inhibitors, optical brightening agents, odorous substances, dyes and formulating aids such as sodium sulfate, by weight of the total weight of the composition. Exact specifications applicable to these additional ingredients are known to the person skilled in the art and therefore require no further description here.

The 2-methyl- and 2-hydroxymethyl-serine-N,N-diacetic acids and their derivatives (I) forming the subject of the present invention have excellent complexing properties and are at least as efficient, in this respect, as conventional complexing agents such as nitrilotriacetic acid and ethylenediaminetetraacetic acid. Also, in their capacity as builders in detergents and cleaning compositions for improving white washing efficiency and the prevention of deposits on the fabric, the compounds I The 2-methyl- and 2-hydroxymethyl-serine-N,N-diacetic acids and their derivatives (I) forming the subject of the present invention have excellent complexing properties and are at least as efficient, in this respect, as conventional complexing agents such as nitrilotriacetic acid and ethylenediaminetetraacetic acid. Also, in their capacity as builders in detergents and cleaning compositions for improving white washing efficiency and the prevention of deposits on the fabric, the compounds I are comparable to, say, nitrilotriacetic acid or ethylenediaminetetraacetic acid. However, they are clearly superior as regards bleach stabilization; and another advantage of compounds I is their biological degradability.

EXAMPLES

All percentages are by weight unless otherwise stated.

EXAMPLE 1

Preparation of 2-hydroxymethyl-serine-N,N-diacetic acid by procedure (a).

To 100 g of a 30% aqueous formaldehyde solution (corresponding to 1.0 mole of $CH_2O$) there was added dropwise, at 20°–25° C. over a period of 75 minutes, a solution of 67 g (0.5 mole) of 2-hydroxymethyl-serine in 250 g of water, which solution had previously been adjusted to pH 8.5 by the addition of 37 g of 40% aqueous sodium hydroxide solution. Stirring was continued for 30 minutes at the temperature stated and the solution was then cooled to 15°-20° C., after which 27 g (1.0 mole) of anhydrous hydrogen cyanide were added dropwise over 90 minutes. Stirring was then continued for 30 minutes at 30° C.

The resulting solution of 2-hydroxymethyl-serine-N,N-diacetonitrile was added dropwise to 101 g of 40% aqueous caustic soda over a period of 1 hour and at a temperature of 80°-100° C. Stirring was continued for 3 hours at 100° C., at which point the liberation of ammonia was found to have ceased. There were obtained 487 g of a clear, yellowish, 30% aqueous solution of the trisodium salt of 2-hydroxymethyl-serine-N,N-diacetic acid.

This trisodium salt solution was placed in a vacuum produced by a water-jet vacuum pump to distill off water until the solids content was approximately 50%. Its pH was then adjusted to 2 with hydrobromic acid. The solution was poured into 4 times its volume of methanol, and the resulting precipitate was filtered off and rewashed with methanol. After drying, there were obtained 98 g of 2-hydroxymethyl-serine-N,N-diacetic acid (78% of theory, based on 2-hydroxymethyl-serine).

EXAMPLE 2

Preparation of 2-hydroxymethyl-serine-N,N-diacetic acid by procedure (c)

To a solution of 45 g (0.5 mole) of 1,3-dihydroxyacetone in 100 g of water there was added dropwise, over a period of 30 minutes and at 25° C., a solution of 66.6 g (0.5 mole) of iminodiacetic acid in 120 g of water, which solution had previously been adjusted to pH 7 by the addition of 50 g of 40% aqueous caustic soda. The solution was then cooled to 15°-20° C., and 13.6 g (0.5 mole) of anhydrous hydrogen cyanide were added dropwise over 45 minutes. Stirring was then continued for 5 hours at 30° C.

90 g of 40% aqueous caustic soda were added to the resulting solution of 2-hydroxymethyl-serinenitrile-N,N-diacetic acid, and the mixture was heated at 90° C. for 4 hours.

From the resulting orange-colored solution of the trisodium salt of 2-hydroxymethyl-serine-N,N-diacetic acid there was obtained the free acid in a manner similar to that described in Example 1 in a yield of 60% of theory, based on the 1,3-dihydroxyacetone.

EXAMPLE 3

Preparation of 2-hydroxymethyl-serine-N,N-diacetic acid by procedure (d)

To a solution of 134 g (1.0 mole) of nitrilotriacetonitrile in 450 g of ethanol, to which triethylamine had previously been added to adjust the pH to 9.5 (as determined on a sample in 10% aqueous solution), there were added dropwise, over a period of 4 hours and at a temperature of 75° C., 250 g of a 30% aqueous formaldehyde solution (corresponding to 2.5 moles of $CH_2O$) whilst keeping the pH constant. Stirring was continued for 4 hours at the temperature stated, and the resulting solution of 2,2-dihydroxymethyl-nitrilotriacetonitrile was added dropwise, over 30 minutes, to 300 g of 40% aqueous caustic soda heated at 100° C. Liberation of ammonia ceased after a further 4 hours at 100° C.

From the resulting solution of the trisodium salt of 2-hydroxymethylserine-N,N-diacetic acid there was obtained the free acid in a manner similar to that described in Example 1 and in a yield of 51% of theory based on the nitrilotriacetonitrile.

EXAMPLE 4

Preparation of 2-methylserine-N,N-diacetic acid by procedure (a)

To 100 g of a 30% aqueous formaldehyde solution (corresponding to 1.0 mole of $CH_2O$) there was added dropwise, at 20°-25° C. over a period of 75 minutes, a solution of 59 g (0.5 mole) of 2-methylserine in 250 ml of water, which solution had previously been adjusted to pH 8.5 by the addition of 37 g of 40% aqueous sodium hydroxide solution. Stirring was continued for 30 minutes at the temperature stated and the solution was then cooled to 15°-20° C., and 27 g (1.0 mole) of anhydrous hydrogen cyanide were added dropwise over 90 minutes. Stirring was then continued for 30 minutes at 30° C.

The resulting solution of 2-methylserine-N,N-diacetonitrile was added dropwise to 102 g of 40% aqueous caustic soda over a period of 1 hour and at a temperature of 80°-100° C. Stirring was continued for 3 hours at 100° C., at which point the liberation of ammonia was found to have ceased. There were obtained 472 g of a clear, yellowish, 30% aqueous solution of the trisodium salt of 2-methyl-serine-N,N-diacetic acid.

This trisodium salt solution was placed in a vacuum produced by a water-jet vacuum pump to distill off water until the solids content was approximately 50%. Its pH was then adjusted to 2 with concentrated hydrochloric acid. The solution was poured into 4 times its volume of methanol, and the resulting precipitate was filtered off and rewashed with methanol. After drying, there were obtained 96 g of 2-methylserine-N,N-diacetic acid (82% of theory, based on 2-methylserine).

EXAMPLE 5

Preparation of 2-methylserine-N,N-diacetic acid by procedure (c)

To a solution of 37 g (0.5 mole) of hydroxyacetone in 100 g of water there was added dropwise, over a period of 30 minutes and at 25° C., a solution of 66.6 g (0.5 mole) of iminodiacetic acid in 120 g of water, which had previously been adjusted to pH 7 by the addition of 50 g of 40% aqueous caustic soda. The solution was then cooled to 15°-20° C., and 13.6 g (0.5 mole) of anhydrous hydrogen cyanide were added dropwise over 45 minutes. Stirring was then continued for 5 hours at 30° C. 90 g of 40% aqueous caustic soda were added to the resulting solution of 2-methylserinenitrile-N,N-diacetic acid, and the mixture was heated at 90° C. for 4 hours, after which the liberation of ammonia was found to have ceased.

From the resulting orange-colored solution of the trisodium salt of 2-methylserine-N,N-diacetic acid there was obtained the free acid in a manner similar to that described in Example 1 and in a yield of 61% of theory, based on hydroxyacetone.

Properties for Industrial Applications

The industrial properties determined on the 2-methyl- and 2-hydroxymethyl-serine-N,N-diacetic acids and derivatives thereof (I) of the invention were their calcium-binding power, their ability to stabilize sodium perborate and their ability to inhibit incrustations in detergent formulations.

A) Determination of calcium-binding power

The inhibiting action of complexing or dispersing agents on the precipitation of calcium carbonate is determined by turbidimetric titration. The substance under test is titrated with calcium acetate solution in the presence of sodium carbonate. The end point is indicated by the formation of the calcium carbonate precipitate. The use of an adequate amount of sodium carbonate ensures that the analysis results stay correct even if the effect is due not only to complexing of calcium ions but also to the dispersion of calcium carbonate.

During titration, variation in transparency is monitored using a fiber-optical photometer. This involves transmitting light through glass fibers to cause it to pass through the solution before impinging on a mirror and measuring the intensity of the light reflected from the mirror.

The test was carried out on a solution of 1.0 g of 2-hydroxymethyl-serine-N,N-diacetic acid or 1.0 g of 2-methylserine-N,N-diacetic acid in 100 ml of distilled water which had been adjusted to pH 10 with 1N caustic soda solution. 10 ml of 10% sodium carbonate solution were then added. Keeping its pH at 11, the test solution was automatically titrated with a 0.25 molar aqueous calcium acetate solution at 20° C. Titration was repeated at pH 10 and a temperature of 80° C. The results are given in the Table below, which lists the amounts of calcium carbonate complexed in mg per g of complexing agent, as calculated using the following equation:

mg of $CaCO_3$/g of complexing agent = amount of $Ca(OAc)_2$ consumed in ml $\times$ 25.

B) Determination of the stabilizing effect on sodium perborate in washing liquids The hydrogen peroxide providing the bleaching effect in detergent formulations containing sodium perborate is catalytically decomposed by heavy metal ions (Fe, Cu, Mn). This can be prevented by complexing the said heavy metal ions. The stabilizing effect of complexing agents on peroxide is measured by determining the residual peroxide content in a washing liquid containing heavy metal ions after this has been kept at elevated temperature for a certain period of time.

The content of hydrogen peroxide in the washing liquid before and after standing at 60° or 80° C. was determined by titration with potassium permanganate in acid solution. The results listed in the Table below give the percentage of $H_2O_2$ still present in the liquid after standing at elevated temperature.

Tests on the stabilization of perborate were carried out using two detergent formulations (1) and (2), decomposition of the perborate on standing at elevated temperature being effected by the addition of heavy metal catalysts (2.5 ppm of a mixture containing 2 ppm of $Fe^{3+}$, 0.25 ppm of $Cu^{2+}$ and 0.25 ppm of $Mn^{2+}$):

(1) Composition of the high-phosphate formulation
19.3% sodium-$C_{12}$-alkylbenzene sulfonate (50% aqueous solution)
15.4% sodium perborate tetrahydrate
30.8% sodium triphosphate
2.6% 50:50 w/w maleic acid/acrylic acid copolymer (av. mol. wt. 50,000)
31.0% anhydrous sodium sulfate
0.9% complexing agent of the invention or comparative substance The detergent concentration was 6.5 g/l using water of 25° dH. The washing liquid was allowed to stand for 2 hours at 80° C.

(2) Composition of the low-phosphate formulation
15% sodium-$C_{12}$-alkylbenzene sulfonate (50% aqueous solution)
5% adduct of 11 moles of ethylene oxide with 1 mole of tallow fat alcohol
20% sodium perborate tetrahydrate
6% sodium metasilicate.$5H_2O$
1.25% magnesium silicate
20% sodium triphosphate
31.75% anhydrous sodium sulfate
1% complexing agent of the invention or comparative substance The detergent concentration was 8 g/l using water of 25° dH. The washing liquid was allowed to stand for 1 hour at 60° C.

C) Determination of inhibition of incrustation

A measure of the amount of water-hardening salts which are deposited on the textile fabric during washing is the weight of the ash which remains after incineration of the washed fabric. The builders added to the detergent formulations serve to minimize such incrustation.

The percentages of ash listed in the Table below are based on the weight of the dry test fabric prior to washing and were determined by the usual method of incineration in a muffle furnace at 700° C.

The incrustation was examined under the following test conditions:

Apparatus: Launder-O-meter (Atlas, Chicago, U.S.A.)
Number of washes: 15
Washing liquid: 250 ml using water containing 4 mmoles of hardening salts per liter (Ca/Mg 4:1)
Duration of wash: 30 minutes at 60° C. (incl. heat-up time)
Detergent concentration: 8 g/l
Test fabric: 10 g of cotton and 10 g of cotton terry
The detergent formulation used was as follows:
12.5% sodium-$C_{12}$-alkylbenzene sulfonate (50% aqueous soln.)
4.7% adduct of 7 moles of ethylene oxide with 1 mole of$C_{13}/C_{15}$-oxoalcohol
2.8% conventional soap
25% conventional zeolite A
5% sodium salt of a 70:30 w/w acrylic acid/maleic acid copolymer having an average mol. wt. of 70,000
4% sodium disilicate
1% magnesium silicate
20% sodium perborate tetrahydrate
16% anhydrous sodium sulfate
1% tylose
8% complexing agent of the invention or comparative substance in the form of the sodium salt.

The Table below lists the results of test A) to C), in which the properties of the novel complexing agents 2-hydroxymethyl-serine-N,N-diacetic acid (Ia) and 2-methylserine-N,N-diacetic acid (Ib), in the form of the acids or their trisodium salts, are compared with those of the conventional complexing agents nitrilotriacetic acid (NTA) and ethylene-diaminetetraacetic acid (EDTA).

The compounds Ia and Ib of the invention provide similar values to NTA and EDTA as regards their calcium-binding power and the inhibition of incrustations, but they are clearly superior to the conventional complexing agents in their ability to stabilize sodium perborate.

alkyl or $C_1$–$C_4$-hydroxyalkyl groups and Z denotes hydrogen or hydroxyl.

2. A method of complexing heavy metal ions and alkaline earth metal ions, comprising: contacting an aqueous solution of the compound of claim 1 with said metal ions.

TABLE

| Complexing agent | Test A CALCIUM-BINDING POWER [mg $CaCo_3$/g of complexing agent] | | Test B STABILIZATION OF SODIUM PERBORATE [Percentage of residual $H_2O_2$] Formulation No. | | Test C INHIBITION OF INCRUSTATION [Percentage of ash] | |
|---|---|---|---|---|---|---|
| | 20° C./pH 11 | 80° C./pH 10 | (1) | (2) | Cotton | Cotton terry |
| Ia | 265 | 250 | 76 | 83 | 0.47 | 0.69 |
| Ib | 320 | 270 | 81 | 83 | 0.54 | 0.54 |
| NTA* | 405 | 435 | 24.5 | 32.5 | 0.49 | 0,54 |
| EDTA* | 315 | 320 | 20 | 34 | (not measured) | |
| none | — | — | — | — | 0,74 | 2.33 |

*for comparison

We claim:

1. 2-Methyl- and 2-hydroxymethyl-serine-N,N-diacetic acid and derivatives thereof of the general formula I

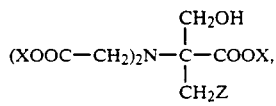

in which X denotes hydrogen, alkali metal or ammonium which may or may not be substituted by $C_1$–$C_4$-

3. A method of washing or cleaning comprising: contacting an article to be washed or cleaned with an aqueous composition containing the compound of claim 1 and a detergent or bleach.

4. A composition for complexing heavy metal ions or alkaline earth metal ions containing from 0.01 to 99% w/w, based on the total weight of the composition, of one or more of the compounds of the general formula I as claimed in claim 1.

5. A detergent or cleaning composition containing from 0.01 to 20% w/w, based on the total weight of the composition, of one or more of the compounds of the general formula I as claimed in claim 1.